United States Patent
Kim et al.

(10) Patent No.: US 8,306,759 B2
(45) Date of Patent: Nov. 6, 2012

(54) APPARATUS AND METHOD FOR CALCULATING TRANSIENT-BASED FATIGUE USAGE FACTOR USING CHARACTERISTIC FATIGUE USAGE CURVE

(75) Inventors: Wan Jae Kim, Daejeon (KR); Jong Jooh Kwon, Daejeon (KR)

(73) Assignee: Korea Hydro & Nuclear Power Co., Ltd., Seoul (KR)

( * ) Notice: Subject to any disclaimer, the term of this patent is extended or adjusted under 35 U.S.C. 154(b) by 336 days.

(21) Appl. No.: 12/761,354

(22) Filed: Apr. 15, 2010

(65) Prior Publication Data

US 2011/0077873 A1    Mar. 31, 2011

(30) Foreign Application Priority Data

Sep. 30, 2009  (KR) .................. 10-2009-0093234

(51) Int. Cl.
*G06F 19/00* (2011.01)

(52) U.S. Cl. ......... 702/34; 702/42; 415/137; 415/209.4; 415/134; 415/142; 415/213.1; 415/223

(58) Field of Classification Search .............. 702/34, 702/42, 179, 184; 415/137, 209.4, 191, 209.3, 415/134, 142, 213.1, 223, 200
See application file for complete search history.

(56) References Cited

U.S. PATENT DOCUMENTS

| | | | | |
|---|---|---|---|---|
| 4,908,775 | A * | 3/1990 | Palusamy et al. | 702/34 |
| 6,907,791 | B2 * | 6/2005 | Choe et al. | 73/794 |
| 7,945,429 | B2 * | 5/2011 | Miyashita et al. | 703/1 |
| 8,083,471 | B2 * | 12/2011 | Black et al. | 415/142 |
| 2004/0079164 | A1 * | 4/2004 | Choe et al. | 73/808 |
| 2008/0243446 | A1 * | 10/2008 | Miyashita et al. | 703/1 |
| 2010/0235108 | A1 * | 9/2010 | Adams et al. | 702/34 |
| 2011/0313726 | A1 * | 12/2011 | Parthasarathy et al. | 702/179 |

* cited by examiner

*Primary Examiner* — Carol Tsai
(74) *Attorney, Agent, or Firm* — Edwards Wildman Palmer LLP

(57) ABSTRACT

The present invention relates to an apparatus and a method for calculating a fatigue usage factor with respect to fatigue generated in the material of a mechanical device depending upon changes of an operation environment during operation of the mechanical device. A fatigue usage factor $U_{OP.cyc,transient\,n}$, which is based on the operation-transient state n, is calculated by multiplying a fatigue usage factor based on a design-transient state $U_{DSGN.cyc,transient\,n}$ by the value of a characteristic fatigue usage factor F (k) as shown in the following equation:

$$U_{OP.cyc,transient\,n} = F(k) \times U_{DSGN.cyc,transient\,n}$$

Since a characteristic fatigue usage factor curve devised in accordance the present invention uses the characteristic fatigue usage factor curve obtained on the basis of the operation-transient state when calculating a transient-based fatigue usage factor, it is possible to much more accurately calculate the fatigue usage factor with respect to any operation-transient state of the mechanical device compared with the prior art.

10 Claims, 3 Drawing Sheets

APPARATUS AND METHOD FOR CALCULATING TRANSIENT-BASED FATIGUE USAGE FACTOR USING CHARACTERISTIC FATIGUE USAGE CURVE

BACKGROUND OF THE INVENTION

1. Field of the Invention

The present invention relates to an apparatus and a method for calculating a fatigue usage factor with respect to fatigue generated in the material of a mechanical device depending upon changes of an operation environment during operation of the mechanical device, and more particularly to an apparatus and a method for calculating a fatigue usage factor at an increased accuracy by reflecting any actual changes of the operation environment into the calculation of the fatigue usage factor.

2. Description of the Related Art

In general, a mechanical device is affected by changes of operation parameters, such as temperature, pressure, flow rate or the like, in accordance with operational conditions while being operated, which may cause fatigue in the material constituting the mechanical device. Such fatigue can be numerically calculated through engineering calculations, and on the basis of that a lifespan of the mechanical device can be predicted.

However, in a method for numerically calculating fatigue generated in the mechanical device using conventional technologies, a value of fatigue has been overestimated. Therefore, it is noted that the expected lifespan of the mechanical device which is calculated on the basis of the overestimated fatigue value may be shortened.

Equation 1 refers to a formula for calculating a cumulative fatigue usage factor with respect to fatigue generated in the mechanical device. The cumulative fatigue usage factor is represented by a sum of each fatigue usage factor to be calculated for respective transient states (1, 2, ..., n). That is, $$\sum_{1}^{n} = U_{transient1} + U_{transient2} + \ldots + U_{transient\ n} \quad (1)$$

wherein "$\Sigma U_{transient\ n}$" denotes the cumulative fatigue usage factor at an arbitrary transient state n.

The term "transient" refers to a status where the operation parameters, such as temperature, pressure, flow rate or the like, are continuously varying in accordance with lapse of time due to changes of the operational condition of the mechanical device.

Equation 2 is a formula for calculating a fatigue usage factor according to the conventional calculation method. The cumulative fatigue usage factor at an arbitrary transient state n is calculated by adding a fatigue usage factor, which is calculated on the basis of a design-transient state, to a cumulative fatigue usage factor which is accumulated till the occurrence of the arbitrary transient state n. That is, $$\Sigma U_{transient\ n} = \Sigma U_{0.transient\ n} + U_{DSGN.cyc.transient\ n} \quad (2)$$

wherein "$\Sigma U_{transient\ n}$" refers to a cumulative fatigue usage factor at an arbitrary transient state n, "$\Sigma U_{0.transient\ n}$" denotes a cumulative fatigue usage factor accumulated till the occurrence of the arbitrary transient state n, and "$U_{DSGN.cyc.transient\ n}$" means a fatigue usage factor calculated on the basis of condition of a design-transient state.

The term "design-transient state" is a transient status defined at the design stage of the mechanical device, which refers to changes of the operation parameters expected to be made during the operation period.

In the conventional calculation method hereinabove, as shown in Equation 2, since the fatigue usage factor which corresponds to the design-transient state is calculated and used even if any operation-transient state occurs, the calculated value of the fatigue usage factor might be greater than that of the actual fatigue usage factor. Consequently, it has drawbacks in that the cumulative fatigue usage factor according to Equation 1 increases, and simultaneously the expected lifespan of the mechanical device is shortened.

SUMMARY OF THE INVENTION

Therefore, the present invention has been made in view of the above problems, and it is an object of the present invention to provide an apparatus and a method for calculating a transient-based fatigue usage factor which is lower than a fatigue usage factor based on a design-transient state, and then can calculate an accurate fatigue usage factor by calculating a characteristic fatigue usage factor on the basis of an operation-transient state.

Through a number of researches on the effect of changes of the operation environment during operation of the mechanical device, inventors of the present invention have retrieved a characteristic fatigue usage factor curve which can accurately calculate the fatigue generated in the mechanical device in consideration of the effect of changes of the operation environment while the mechanical device is operating.

The present invention allows a fatigue usage factor, which is a numerically represented fatigue index, to be accurately calculated by obtaining the fatigue usage factor using the characteristic fatigue usage factor curve. More particularly, in order to reflect the actual changes of the operation parameters upon the design of the mechanical device, a new fatigue usage factor is calculated by multiplying a fatigue usage factor which is calculated from expectation of changes of the operation parameter by a predetermined rate, and then such a process is repeatedly performed with respect to major operation parameters to obtain a characteristic fatigue usage factor curve. As a result, with use of the characteristic fatigue usage factor curve as the above, a fatigue usage factor which is generated in the material of the mechanical device due to any feasible changes of the operation environment during operation of the mechanical device, can be calculated at a much more increased accuracy.

In accordance with one aspect of the present invention, the above and other objects can be accomplished by the provision of an apparatus for calculating a fatigue usage factor to analyze the effect of a transient state created during operation of a mechanical device on a fatigue index in the material of the mechanical device, the apparatus including a transient state input unit to input information related to the transient state created during operation of the mechanical device; a characteristic fatigue usage factor calculating unit to calculate a characteristic fatigue usage factor based on the operation-transient state; a characteristic fatigue usage factor curve generation unit to generate a characteristic fatigue usage factor curve using the characteristic fatigue usage factor calculated by the characteristic fatigue usage factor calculating unit; a fatigue usage factor calculating unit to calculate a fatigue usage factor based on the operation-transient state; a cumulative fatigue usage factor calculating unit to calculate a cumulative fatigue usage factor based on the operation-transient state using the fatigue usage factor calculated by the fatigue usage factor calculating unit; and a cumulative fatigue usage factor output unit to output the cumulative fatigue usage factor calculated by the cumulative fatigue usage factor calculating unit.

In accordance with another aspect of the present invention, there is provided a method to calculate a fatigue usage factor to analyze the effect of a transient state created during operation of a mechanical device on a fatigue index in a material of the mechanical device, the method including the steps of inputting information related to the transient state created during operation of the mechanical device; calculating a characteristic fatigue usage factor based on the operation-transient state; generating a characteristic fatigue usage factor curve using the calculated characteristic fatigue usage factor; calculating a fatigue usage factor based on the operation-transient state; calculating a cumulative fatigue usage factor based on the operation-transient state using the calculated fatigue usage factor; and outputting the calculated cumulative fatigue usage factor.

It is advisable to obtain the cumulative fatigue usage factor by adding the fatigue usage factor calculated on the basis of the operation-transient state to the cumulative fatigue usage factor which is accumulated till the occurrence of the transient state.

In addition, the fatigue usage factor based on the operation-transient state is preferably calculated by multiplying the fatigue usage factor based on the design-transient state by the value of the characteristic fatigue usage factor.

Preferably, an equation for calculating the characteristic fatigue usage factor is represented as a ratio of an allowable repetition number based on the design-transient state to an allowable repetition number based on the operation-transient state.

Further, it is preferable to obtain the characteristic fatigue usage factor with respect to the various transient states, and then to generate the characteristic fatigue usage factor curve using the characteristic fatigue usage factor.

Moreover, the characteristic fatigue usage factor corresponding to the characteristic fatigue usage factor is preferably obtained using the generated characteristic fatigue usage factor curve, and the fatigue usage factor based on the operation-transient state is calculated by multiplying the fatigue usage factor based on the design-transient state by the value of the characteristic fatigue usage factor.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, an apparatus and a method for calculating a transient-based fatigue usage factor in accordance with the present invention will be described in detail.

Here, the apparatus for calculating a fatigue usage factor in accordance with the present invention is devised to analyze the effect of a transient state created during operation of a mechanical device on a fatigue index in the material of the mechanical device.

Figure 1:
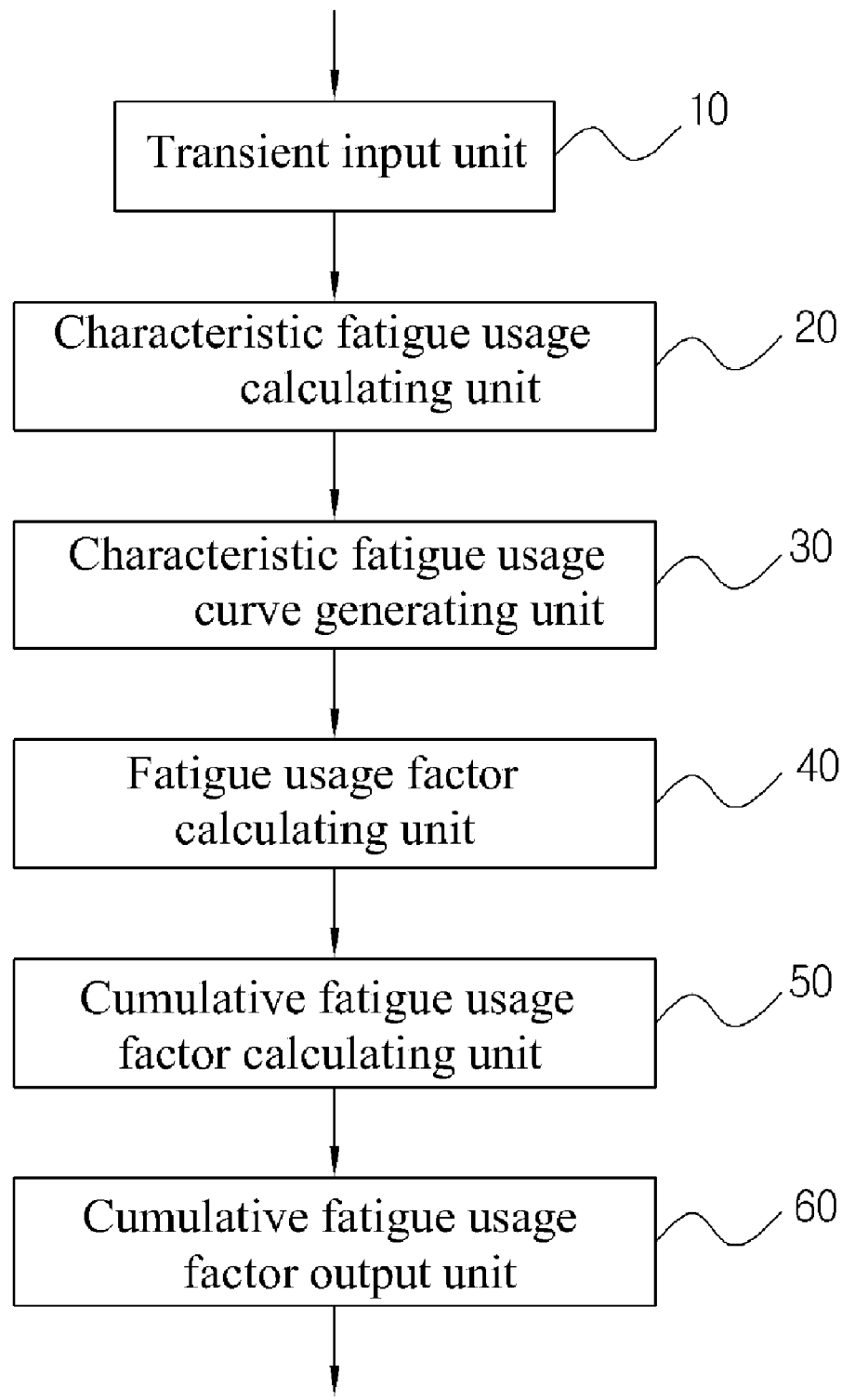
FIG. 1 is a block diagram of an apparatus for calculating a fatigue usage factor in accordance with the present invention.

FIG. 1 illustrates a block diagram of an apparatus for calculating a fatigue usage factor in accordance with the present invention.

Referring to FIG. 1, reference numeral 10 refers to a transient state input unit and serves to put into information related to a transient state created during operation of the mechanical device. Reference numeral 20 represents a characteristic fatigue usage factor calculating unit to calculate a characteristic fatigue usage factor based on an operation-transient state. Reference numeral 30 denotes a characteristic fatigue usage factor curve generating unit to generate a characteristic fatigue usage factor curve using the characteristic fatigue usage factor calculated by the characteristic fatigue usage factor calculating unit 20. Further, reference numeral 40 represents a fatigue usage factor calculating unit to calculate a fatigue usage factor based on the operation-transient state, reference numeral 50 refers to a cumulative fatigue usage factor calculating unit to calculate a cumulative fatigue usage factor based on the operation-transient state using the fatigue usage factor calculated by the fatigue usage factor calculating unit 40, and reference numeral 60 denotes a cumulative fatigue usage factor output unit to output the cumulative fatigue usage factor calculated by the cumulative fatigue usage factor calculating unit 50.

The Equation 3 refers to a fatigue usage factor calculation formula in consideration of an actual operation-transient state.

$$\Sigma U_{transient\ n.OP} = \Sigma U_{0.transient\ n} + U_{DSGN.cyc.transient\ n} \quad (3)$$

Here, a cumulative fatigue usage factor $\Sigma U_{transient\ n.OP}$, which is calculated on the basis of an arbitrary operation-transient state n, is represented by a sum of a cumulative fatigue usage factor $\Sigma U_{0.transient\ n}$ accumulated till the occurrence of the operation-transient state n and a fatigue usage factor $U_{OP.cyc.transient\ n}$ at the occurrence of the operation-transient state n.

At this point, the fatigue usage factor $U_{OP.cyc.transient\ n}$ derived in the present invention is calculated from Equation 4-1, which is based on the operation-transient state n.

$$U_{OP.cyc.transient\ n} = F(k) \times U_{DSGN.cyc.transient\ n} \quad (4\text{-}1)$$

As can be seen in Equation 4-1, the operation-transient based fatigue usage factor $U_{OP.cyc.transient\ n}$ is obtained by multiplying a fatigue usage factor based on a design-transient state $U_{DSGN.cyc.transient\ n}$ by the value of a characteristic fatigue usage factor F (k). The operation-transient based fatigue usage factor $U_{OP.cyc.transient\ n}$ and the design-transient based fatigue usage factor $U_{DSGN.cyc.transient\ n}$ in Equation 4-1 are represented by the following Equations 5 and 6, respectively. Accordingly, a formula to calculate the characteristic fatigue usage factor F (k) may be expressed as Equation 7 by substituting Equations 5 and 6 into Equation 4-1.

Meanwhile, k in Equation 4-2 represents a ratio of time derivatives of temperature. That is, $$k = \frac{\dot{T}}{\dot{T}_{DT}} \quad (4\text{-}2)$$

wherein "$\dot{T}$" is a time derivative of temperature at a corresponding operation-transient state, while "$\dot{T}_{DT}$" is a time derivative of temperature at a design-transient state.

Equation 5 is an equation for calculating a fatigue usage factor based on the occurrence of a design-transient state. A design-transient based fatigue usage factor $U_{DSGN.cyc}$ is calculated by dividing a repetition number of the transient state $N_{DSGN}$ which is previously determined at the time of a design by an allowable repetition number $N_{Allow,DSGN}$ which is calculated on the basis of occurrence of a design-transient state.

$$U_{DSGN.cyc} = \frac{N_{DSGN}}{N_{Allow,DSGN}} \quad (5)$$

Equation 6 represents an equation for calculating a fatigue usage factor based on the occurrence of an operation-transient state. An operation-transient based fatigue usage factor $U_{OP.cyc}$ is calculated by dividing a repetition number of the transient state $N_{DSGN}$ which is previously determined upon design by an allowable repetition number $N_{Allow,OP}$ which is calculated on the basis of the occurrence of an operation-transient state.

$$U_{OP.cyc} = \frac{N_{DSGN}}{N_{Allow,OP}} \quad (6)$$

Generally, since the design-transient state has a greater impact on the creation of material fatigue than the actual operation-transient state, the allowable repetition number based on the design-transient state is smaller than that based on the operation-transient state. Accordingly, the value of the design-transient based fatigue usage factor of Equation 5 is greater than that of the operation-transient based fatigue usage factor of Equation 6.

Equation 7 refers to the characteristic fatigue usage factor F (k). The characteristic fatigue usage factor F (k) is calculated by dividing the allowable repetition number based on the design-transient state $N_{Allow,DSGN}$ by the allowable repetition number based on the operation-transient state $N_{Allow,OP}$.

$$F(k) = \frac{N_{Allow,DSGN}}{N_{Allow,OP}} \quad (7)$$

Figure 3:
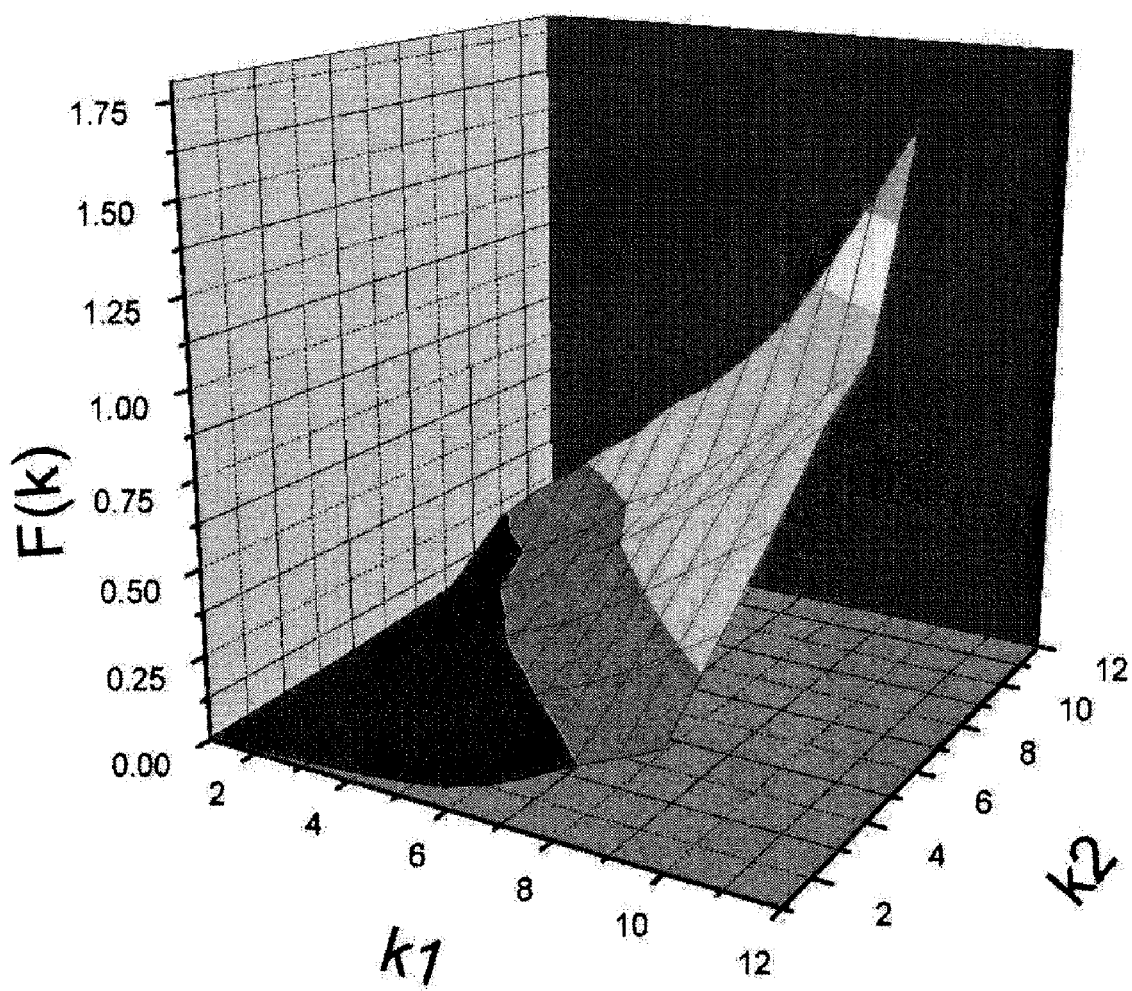
FIG. 3 is a view illustrating an example of a characteristic fatigue usage factor curve obtained with respect to a specific operation-transient state.

FIG. 3 is a view illustrating an example of a characteristic fatigue usage factor curve obtained with respect to a specific operation-transient state. The operation-transient based fatigue usage factor $U_{OP.cyc,transient\,n}$ is obtained through the characteristic fatigue usage factor calculating unit 20 in FIG. 1. As shown in Equation 4-1, the operation-transient based fatigue usage factor $U_{OP.cyc,transient\,n}$ is calculated by multiplying the characteristic fatigue usage factor F (k), which is determined by the values of k1 and k2, by the design-transient based fatigue usage factor $N_{DSGN.cyc,transinet\,n}$. In other words, a ratio k of the time derivative of the temperature variations is calculated by dividing a various feasible time derivative of temperature variations ($\dot{T}$) by an actual time derivative of temperature variations ($\dot{T}_{DT}$) in the material. Next, the characteristic fatigue usage factor F (k) in Equation 7 is obtained by using the calculated value of the ratio k, and then the characteristic fatigue usage factor curve is drawn as shown in FIG. 3.

Hereinafter, a method for calculating a fatigue usage factor in accordance with the present invention will be described.

Figure 2:
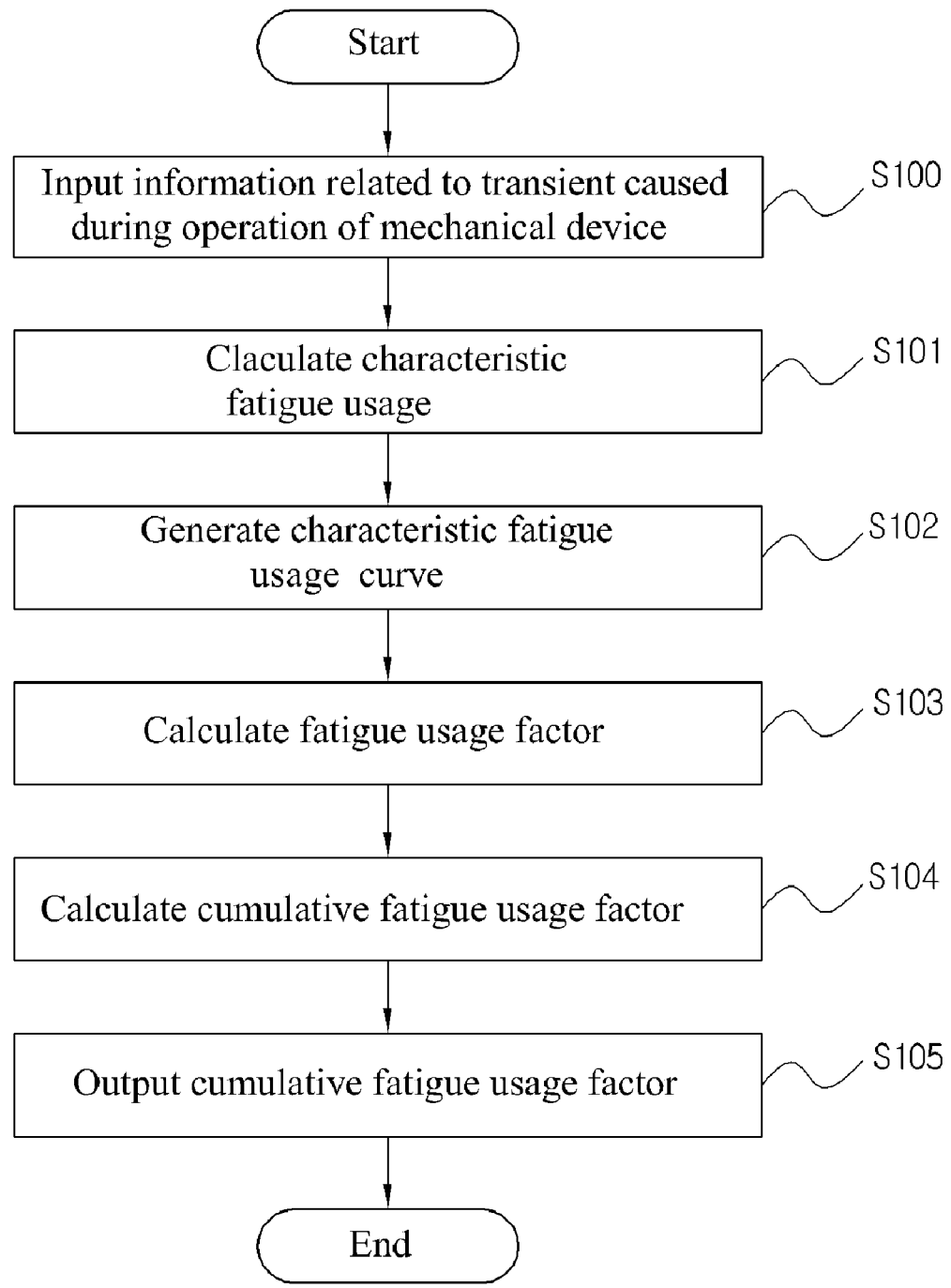
FIG. 2 is a flow chart illustrating an operation of the apparatus for calculating the fatigue usage factor in accordance with the present invention.

FIG. 2 is a flow chart illustrating an operation of the fatigue usage factor calculating apparatus in accordance with the present invention.

The method for calculating a fatigue usage factor in accordance with the present invention is designed to calculate the effect of the transient state, which is created during the operation of the mechanical device, on the fatigue in the material of the mechanical device.

First, information related to a transient state created during the operation of the mechanical device is inputted (S100). A characteristic fatigue usage factor based on the operation-transient state is calculated (S101), and a characteristic fatigue usage factor curve is then generated using the characteristic fatigue usage factor being calculated as the above (S102).

Next, a fatigue usage factor based on the operation-transient state is calculated (S103), a cumulative fatigue usage factor based on the operation-transient state is calculated using the calculated fatigue usage factor (S104), and the calculated cumulative fatigue usage factor is then outputted (S105). In addition, the cumulative fatigue usage factor after the transient state occurs can be calculated by adding a fatigue usage factor based on the operation-transient state to a cumulative fatigue usage factor which is accumulated till the occurrence of the transient state.

Further, it is possible to calculate the operation-transient based fatigue usage factor by multiplying the design-transient based fatigue usage factor by the value of the characteristic fatigue usage factor.

In addition, the equation for calculating the characteristic fatigue usage factor can be represented as a ratio of an allowable repetition number calculated on the basis of the design-transient state to an allowable repetition number based on the operation-transient state.

It should be appreciated that the characteristic fatigue usage factor curve can be also generated using characteristic fatigue usage factors which are calculated with respect to various transient states.

Moreover, the value of the characteristic fatigue usage factor which corresponds to the characteristic fatigue usage factor can be obtained using the characteristic fatigue usage factor curve generated as the above. Then, with multiplication of the design-transient based fatigue usage factor by the characteristic fatigue usage factor, the operation-transient based fatigue usage factor can be calculated accordingly.

As is apparent from the above description, the present invention provides an apparatus and a method for calculating a fatigue usage factor with respect to fatigue generated in the material of the mechanical device due to the operation-transient state. The inventive apparatus and method are devised to calculate a reasonable fatigue usage factor by removing the excessive conservatism of conventional methods which have used the design-transient state. With development of an algorithm using the characteristic fatigue usage factor curve which is capable of reflecting the operation-transient state, it is possible to remarkably improve the calculation accuracy of the fatigue usage factor of the mechanical device.

It should be noted that the present invention can assist development of technologies related to fatigue monitoring and estimation of the mechanical device, and is applicable to all the fields of power generation, such as a nuclear power plant, thermal power plant or the like, which creates a load boundary of high temperature and pressure.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. An apparatus for calculating a fatigue usage factor, comprising:
   a transient state input unit to input information related to a transient state created during operation of the mechanical device;
   a characteristic fatigue usage factor calculating unit to calculate a characteristic fatigue usage factor based on an operation-transient state;
   a characteristic fatigue usage factor curve generation unit to generate a characteristic fatigue usage factor curve using the characteristic fatigue usage factor calculated by the characteristic fatigue usage factor calculating unit;
   a fatigue usage factor calculating unit to calculate a fatigue usage factor based on the operation-transient state;
   a cumulative fatigue usage factor calculating unit to calculate a cumulative fatigue usage factor based on the operation-transient state using the fatigue usage factor calculated by the fatigue usage factor calculating unit; and
   a cumulative fatigue usage factor output unit to output the cumulative fatigue usage factor calculated by the cumulative fatigue usage factor calculating unit to analyze an effect of a transient state created during operation of a mechanical device on a fatigue index in a material of a mechanical device,
   wherein
   a value of the characteristic fatigue usage factor which corresponds to the characteristic fatigue usage factor is obtained using the generated characteristic fatigue usage factor curve, and
   the operation-transient based fatigue usage factor is calculated by multiplying a design-transient based fatigue usage factor by the characteristic fatigue usage factor.

2. The apparatus as recited in claim 1, wherein the cumulative fatigue usage factor after the transient state occurs is calculated by adding a fatigue usage factor based on the operation-transient state to a cumulative fatigue usage factor which is accumulated till the occurrence of the transient state.

3. The apparatus as recited in claim 1, wherein the fatigue usage factor based on the operation-transient state is calculated by multiplying a fatigue usage factor based on a design-transient state by the value of the characteristic fatigue usage factor.

4. The apparatus as recited in claim 1, wherein an equation for calculating the characteristic fatigue usage factor is represented as a ratio of an allowable repetition number calculated on the basis of a design-transient state to an allowable repetition number based on the operation-transient state.

5. The apparatus as recited in claim 1, wherein the characteristic fatigue usage factor curve is generated using characteristic fatigue usage factors which are calculated with respect to various transient states.

6. A method for calculating a fatigue usage factor, comprising:
   inputting information related to the transient state created during operation of the mechanical device;
   calculating a characteristic fatigue usage factor based on the operation-transient state;
   generating a characteristic fatigue usage factor curve using the calculated characteristic fatigue usage factor; calculating a fatigue usage factor based on the operation-transient state;
   calculating a cumulative fatigue usage factor based on the operation-transient state using the calculated fatigue usage factor; and
   outputting the calculated cumulative fatigue usage factor to analyze an effect of a transient state created during operation of a mechanical device on a fatigue index in a material of a mechanical device,
   wherein
   a value of the characteristic fatigue usage factor which corresponds to the characteristic fatigue usage factor is obtained using the generated characteristic fatigue usage factor curve, and
   the operation-transient based fatigue usage factor is calculated by multiplying a design-transient based fatigue usage factor by the characteristic fatigue usage factor.

7. The method as recited in claim 6, wherein the cumulative fatigue usage factor after the transient state occurs is calculated by adding a fatigue usage factor based on the operation-transient state to a cumulative fatigue usage factor which is accumulated till the occurrence of the transient state.

8. The method as recited in claim 6, wherein the fatigue usage factor based on the operation-transient state is calculated by multiplying a fatigue usage factor based on a design-transient state by the value of the characteristic fatigue usage factor.

9. The method as recited in claim 6, wherein an equation for calculating the characteristic fatigue usage factor is represented as a ratio of an allowable repetition number calculated on the basis of a design-transient state to an allowable repetition number based on the operation-transient state.

10. The method as recited in claim 6, wherein the characteristic fatigue usage factor curve is generated using characteristic fatigue usage factors which are calculated with respect to various transient states.

* * * * *